US 6,683,179 B2

(12) United States Patent
Bassler et al.

(10) Patent No.: US 6,683,179 B2
(45) Date of Patent: Jan. 27, 2004

(54) PREPARATION OF CAPROLACTAM

(75) Inventors: Peter Bassler, Viernheim (DE); Dieter Baumann, Walldorf (DE); Rolf-Hartmuth Fischer, Heidelberg (DE); Eberhard Fuchs, Frankenthal (DE); Johann-Peter Melder, Böhl-Iggelheim (DE); Frank Ohlbach, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/258,941

(22) PCT Filed: Apr. 30, 2001

(86) PCT No.: PCT/EP01/04837
§ 371 (c)(1),
(2), (4) Date: Oct. 29, 2002

(87) PCT Pub. No.: WO01/83443
PCT Pub. Date: Nov. 8, 2001

(65) Prior Publication Data
US 2003/0105322 A1 Jun. 5, 2003

(30) Foreign Application Priority Data
May 3, 2000 (DE) .......................... 100 21 192

(51) Int. Cl.$^7$ ............................................ C07D 201/08
(52) U.S. Cl. ..................................................... 540/539
(58) Field of Search ........................................ 540/539

(56) References Cited

U.S. PATENT DOCUMENTS

| 5,032,684 A | 7/1991 | Neubauer ................... 540/540 |
| 5,493,021 A | 2/1996 | Barratt et al. ............... 540/539 |
| 5,496,941 A | 3/1996 | Ritz et al. ................... 540/540 |
| 6,030,505 A | 2/2000 | Achhammer et al. ......... 203/49 |
| 6,262,259 B1 | 7/2001 | Cotting et al. .............. 540/539 |
| 6,353,101 B1 * | 3/2002 | Eiermann et al. ........... 540/539 |

FOREIGN PATENT DOCUMENTS

| EP | 943 608 | 9/1999 |
| GB | 969993 | 9/1964 |
| SU | 75 083 | 8/1970 |
| WO | 97/02228 | 1/1997 |
| WO | 98/37063 | 8/1998 |
| WO | 99/47500 | 9/1999 |
| WO | WO 99/65873 | * 12/1999 |

OTHER PUBLICATIONS

Ull.Ency.Ind.Chem.,5Ed,vol.A5,1986, 46–48.
Ency.Chem.Soc.4Ed,vol. 4,1992, 836.

* cited by examiner

Primary Examiner—Bruck Kifle
(74) Attorney, Agent, or Firm—Keil & Weinkauf

(57) ABSTRACT

A process for the preparation of caprolactam is provided, wherein a) a mixture (I) containing 6-aminocapronitrile and water is reacted in the gas phase, in the presence of a catalyst, to give a mixture (II) containing caprolactam, ammonia, water, high-boiling components and low-boiling components, b) ammonia is then removed from the mixture (II) to give a mixture (III) containing caprolactam, water, high-boiling components and low-boiling components, c) water is then removed from the mixture (III) to give a mixture (IV) containing caprolactam, high-boiling components and low-boiling components, and d) a solid (V) containing caprolactam is then obtained from the mixture (IV) by crystallization, the proportion by weight of caprolactam in the solid (V) being greater than in the mixture (IV).

11 Claims, No Drawings

PREPARATION OF CAPROLACTAM

The present invention relates to a process for the preparation of caprolactam, wherein
- a) a mixture (I) containing 6-aminocapronitrile ("ACN") and water is reacted in the gas phase, in the presence of a catalyst, to give a mixture (II) containing caprolactam, ammonia, water, high-boiling components and low-boiling components,
- b) ammonia is then removed from the mixture (II) to give a mixture (III) containing caprolactam, water, high-boiling components and low-boiling components,
- c) water is then removed from the mixture (III) to give a mixture (IV) containing caprolactam, high-boiling components and low-boiling components, and
- d) a solid (V) containing caprolactam is then obtained from the mixture (IV) by crystallization, the proportion by weight of caprolactam in the solid (V) being greater than in the mixture (IV).

Processes for the preparation of caprolactam are generally known.

It is also generally known, for example from Ullmann's Encyclopedia of Industrial Chemistry, 5th Ed., Vol. A5, VCH Verlagsgesellschaft mbH, Weinheim (Germany), 1986, pages 46–48, or Kirk-Othmer, Encyclopedia of Chemical Technology, 4th Ed., Vol. 4, John Wiley & Sons, New York, 1992, page 836, that caprolactam used for the preparation of polymers must have a purity of 99.9 to 99.94%, the main impurity conventionally being water in an amount of 0.04 to 0.1%. Other impurities must only be present in an amount of at most a few ppm.

Thus caprolactam can be prepared by a Beckmann rearrangement of cyclohexanone oxime with sulfuric acid or oleum. After neutralization of the resulting mixture with ammonia, the caprolactam can be obtained from the ammonium sulfate formed as a by-product by extraction with an organic solvent.

Depending on the processes for the preparation of the educts used to prepare the cyclohexanone oxime, such as cyclohexanone and hydroxylammonium sulfate, and on the oximation and rearrangement conditions, the crude caprolactam obtained by a Beckmann rearrangement contains different types and amounts of impurities. Typical impurities in crude caprolactam prepared by a Beckmann rearrangement are C-methylcaprolactams, 6-methylvalerolactam and n-pentylacetamide.

Various processes are described for the purification of crude caprolactam obtained by a Beckmann rearrangement.

According to DE-A-1253716, the crude caprolactam can be purified by hydrogenation in suspension, in the presence of a catalyst and with the addition of an acid.

According to DE-A-1253716, the crude caprolactam can be purified by hydrogenation in suspension, in the presence of a catalyst and with the addition of a base.

DD-A-75083 describes a process for the purification of crude caprolactam in which the crude caprolactam is first distilled and then dissolved in an organic solvent, hydrogenated in the presence of a catalyst and then treated with an ion exchanger.

According to EP-A-411455, the important characteristic quality features of caprolactam can be preserved by hydrogenating the crude caprolactam continuously in a liquid phase process.

Crude caprolactam obtained by the hydroformylation of 3-pentenoic acid and/or its esters to give 5-formylvaleric acid (esters) as main products and 4- and 3-formylvaleric acid (esters) as by-products, separation of this (these) branched formylvaleric acid (esters) by extraction (WO 97/02228) or distillation (WO 97/06126), aminating hydrogenation of 5-formylvaleric acid (esters) to 6-aminocaproic acid (esters) and/or 6-aminocaproic acid amide, and cyclization of 6-aminocaproic acid (esters) or 6-aminocaproic acid amide, contains other typical impurities.

Thus it is known e.g. from WO 99/48867, Example 1, to crystallize crude caprolactam obtained from 5-formylvaleric acid esters, according to WO 98/37063, Example 9, from mixtures of 6-aminocaproic acid, 6-aminocaproic acid amide and corresponding oligomers, by the addition of 10% by weight of water. This crude caprolactam, from which high-boiling and low-boiling components were not separated before crystallization, contained 6345 ppm of N-methylcaprolactam, 100 ppm of 5-methylvalerolactam, 78 ppm of valeramide and other impurities. The crude caprolactam/water melt was homogenized at 50° C. and then cooled to 30° C. The crystals which precipitated out were filtered off and washed 2 to 3 times with aqueous caprolactam. The 5-methylvalerolactam and valeramide contents were reduced to 1 ppm and the N-methylcaprolactam content to 51 ppm. 33.7 g of pure lactam were obtained from 73.6 g of crude lactam (caprolactam yield: 45.8%). The characteristic of the volatile bases (VB) was only achieved by a second crystallization. If high-boiling and low-boiling components were separated from the crude caprolactam before crystallization, according to WO 99/48867, Example 3, the caprolactam yield after crystallization was 52%.

It is further known from WO 99/65873 selectively to adsorb caprolactam from mixtures with 4-ethyl-2-pyrrolidone, 5-methyl-2-piperidone, 3-ethyl-2-pyrrolidone and 3-methyl-2-piperidone or octahydrophenazine on adsorbents like activated carbon, molecular sieves or zeolites to give highly pure caprolactam after desorption. This separation of caprolactam can be followed by crystallization from the melt or crystallization from a solvent.

It is further known to purify, by crystallization, crude caprolactam which, starting from 6-aminocapronitrile, is first hydrolyzed with water to 6-aminocaproic acid, according to WO 98/37063, claim 8. Water and ammonia formed by hydrolysis are then separated off, the 6-aminocaproic acid formed is cyclized and the crude caprolactam obtained is crystallized according to WO 99/48867.

Caprolactam can also be obtained by reacting ACN with water in the liquid phase, in the presence or absence of a catalyst, with the release of ammonia.

In addition to caprolactam, water, ammonia and optionally another liquid diluent, the mixture obtained in this reaction contains impurities boiling above caprolactam ("high-boiling components") and impurities boiling below caprolactam ("low-boiling components").

It is known from the Example in U.S. Pat. No. 496,941 that, after the separation of water, solvent, ammonia, low-boiling component and high-boiling component from a mixture obtained by reacting ACN with water and solvent, a crude caprolactam is obtained with a purity of 99.5%.

Other methods of purification are described for a crude caprolactam obtained from ACN in the liquid phase since the impurities in this type of crude caprolactam is [sic] markedly different from those in a crude caprolactam obtained by other processes, as described in U.S. Pat. No. 5,496,941.

In a first step, according to U.S. Pat. No. 5,496,941, ACN is converted to caprolactam in the liquid phase, low-boiling components, water, ammonia and optionally other solvents are simultaneously separated off, high-boiling components are separated off to give a crude caprolactam with a purity of 99.5%, this crude caprolactam is hydrogenated in the presence of a catalyst, the product obtained is treated with an acidic ion exchanger or sulfuric acid and the resulting product is distilled in the presence of a base.

WO 96/20923 discloses a method of purifying crude caprolactam originating from the liquid phase cyclization of 6-aminocapronitrile with water in the presence of a solvent and heterogeneous catalysts. In this case, crude caprolactam is first hydrogenated, then treated with acidic agents and finally distilled in the presence of alkali. The disadvantage of this method of purification is that three separate reaction steps are required to prepare pure caprolactam.

The cyclization of 6-aminocapronitrile in the gas phase in the presence of water and a catalyst, for example as described in EP-A-659 741, WO 96/22974, DE 19632006, WO 99/47500 or WO 99/28296, gives a crude caprolactam in which the typical impurities are different from those in a crude caprolactam obtained by another process. Examples of typical impurities in a crude caprolactam obtained from ACN in the gas phase are cyanoalkyl- and aminoalkyl-substituted caprolactam derivatives and tetrahydroazepine derivatives, such as N-cyanopentylhexamethyleneimine, N-cyanopentylcaprolactam and N-aminohexylcaprolactam. In pure caprolactam, these impurities contribute to a degradation of the quality characteristics generally known for caprolactam, for example from Ullmann's Encyclopedia of Industrial Chemistry, 5th Ed., Vol. A5, VCH Verlagsgesellschaft mbH, Weinheim (Germany), 1986, pages 46–48, or Kirk-Othmer, Encyclopedia of Chemical Technology, 4th Ed., Vol. 4, John Wiley & Sons, New York, 1992, page 836, such as the values for the free and volatile base [sic] and UV characteristics.

It is an object of the present invention to provide a process which makes it possible to prepare, in high purity and in a technically simple and energy-saving manner, caprolactam which has been obtained from ACN in the gas phase.

We have found that this object is achieved by the process defined at the outset.

In step a), a mixture (I) containing 6-aminocapronitrile, water and optionally liquid diluent is converted in the gas phase, in the presence of a solid which promotes the reaction catalytically, to a mixture (II) containing caprolactam, ammonia, water, optionally liquid diluent, high-boiling components and low-boiling components.

The ACN required for step a) can be obtained from adipodinitrile, as is generally known from Ullmann's Encyclopedia of Industrial Chemistry, 5th Ed., Vol. A5, VCH Verlagsgesellschaft mbH, Weinheim (Germany), 1986, page 46, FIG. 8.

Particularly appropriate here is the partial catalytic hydrogenation of adipodinitrile in the presence of ammonia as solvent and e.g. in the presence of rhodium on magnesium oxide (U.S. Pat. No. 4,601,859), Raney nickel (U.S. Pat. No. 2,762,835, WO 92/21650) or nickel on aluminum oxide (U.S. Pat. No. 2,208,598) as a suspension catalyst or Cu—Co—Zn spinel (DE-B-954416, U.S. Pat. No. 2,257,814) or iron (DE-A-42 35 466) as a fixed bed catalyst, or a process according to U.S. Pat. No. 2,245,129, U.S. Pat. No. 2,301,964, EP-A-150295 or FR-A-2 029 540, or a process described in U.S. Pat. No. 5,496,941.

The adipodinitrile required for this reaction is prepared industrially, e.g. by the double hydrocyanation of butadiene in the presence of nickel-containing catalysts, and is commercially available, e.g. from Aldrich-Chemie Gesellschaft mbH & Co. KG, Steinheim, Germany. The conversion of the mixture (I) to the mixture (II) can be carried out according to EP-A-659 741, WO 96/22974, DE 19632006, WO 99/47500 or WO 99/28296 for example.

The reaction can preferably be carried out in the gas phase at temperatures generally of 200 to 550° C., preferably of 250 to 400° C.; the pressure ranges generally from 0.01 to 10 bar and is preferably atmospheric pressure, it being necessary to ensure that the reaction mixture is predominantly gaseous under the conditions used.

The catalyst loads are usually 0.05 to 2, preferably 0.1 to 1.5 and particularly 0.2 to 1 kg of 6-aminocapronitrile per liter of catalyst volume per hour.

The reaction can be carried out batchwise or, preferably, continuously.

Suitable reactors are advantageously those which are generally known for gas phase reactions on moving or stationary solid catalysts. It is preferred to use a fluidized bed reactor or, preferably, a fixed bed reactor such as a tray reactor, especially a tubular reactor. Combinations of such reactors are also possible.

The amount of water used is generally 1 to 50, preferably 1 to 10 mol per mol of ACN.

The mixture (I) can also contain other organic compounds which are gaseous under the reaction conditions, such as alcohols, amines or aromatic or aliphatic hydrocarbons.

Examples of suitable catalytically active compounds in the catalysts are silicon dioxide in the form of pyrogenic silicon dioxide, silica gel, kieselguhr, quartz or mixtures thereof, copper chromite, preferably aluminum oxide, titanium oxide, preferably titanium dioxide, lanthanum phosphates and lanthanum oxides, as well as mixtures of such compounds.

Aluminum oxide is suitable in any modifications which can be obtained by heating the aluminum hydroxide precursor compounds (gibbsite, boehmite, pseudoboehmite, bayerite and diaspore) at varying temperatures. These include especially gamma- and alpha-aluminum oxide and mixtures thereof.

Titanium dioxide is amorphous and is suitable in any of its modifications, preferably anatase and rutile, and mixtures of such modifications.

Lanthanum phosphates are suitable, individually or in a mixture, in their various modifications, stoichiometric ratios of lanthanum to phosphate unit and degrees of condensation of the phosphate units (monophosphate, oligophosphates such as diphosphates or triphosphates, polyphosphates).

These compounds can be used in the form of powders, chips, grit, strands or tablets (produced by compression). The form of the compounds normally depends on the requirements of the particular reaction procedure, powder or chips advantageously being used in the fluidized bed procedure. In the fixed bed procedure, it is conventional to use tablets or strands with diameters of between 1 mm and 6 mm.

The compounds can be used in the pure form (content of the individual compounds >80% by weight), as a mixture of the abovementioned compounds, in which case the sum of the abovementioned compounds should be >80% by weight, or as a supported catalyst, in which case the abovementioned compounds can be applied to a mechanically and chemically stable support, usually with a high surface area.

The pure compounds may have been prepared by precipitation from aqueous solutions, e.g. titanium dioxide by the sulfate process, or by other processes such as the pyrogenic preparation of fine aluminum oxide, titanium dioxide or zirconium dioxide powders, which are commercially available.

A choice of several methods is available for the preparation of mixtures of the different compounds. The compounds, or their precursor compounds which can be converted to the oxides by calcination, can be prepared e.g. by joint precipitation from solution. A very good distribution of the two compounds used is generally obtained by this method. The compound or precursor mixtures can also be obtained by precipitation of one compound or precursor in the presence of the second compound or precursor present as a suspension of fine particles. Another method consists in mechanically mixing the compound or precursor powders, it being possible for this mixture to be used as a starting material for the production of strands or tablets.

In principle, supported catalysts can be prepared by any of the methods described in the literature. Thus the compounds can be applied to the support in the form of their sols simply by impregnation. The volatile constituents of the sol are conventionally removed from the catalyst by drying and calcination. Such sols are commercially available for titanium dioxide and aluminum oxide.

Another possible way of applying layers of the catalytically active compounds consists in hydrolyzing or pyrolyzing organic or inorganic compounds. Thus a ceramic support can be coated with a thin layer of titanium dioxide by hydrolyzing titanium isopropylate or other Ti alkoxides. Other suitable compounds are $TiCl_4$ and aluminum nitrate, inter alia. Suitable supports are powders, strands or tablets of said compounds themselves or of other stable compounds like steatite or silicon carbide. The supports used can be in a macroporous form in order to improve the material transport.

The reaction can be carried out in the presence of a gas which is inert as regards the conversion of the mixture (I) to the mixture (II), preferably argon and in particular nitrogen. The volume ratio of the inert gas to the ACN, which is gaseous under reaction conditions, can advantageously be up to 100.

In step b), ammonia is removed from the mixture (II) to give a mixture (III) containing caprolactam, water, optionally liquid diluent, high-boiling components and low-boiling components.

In principle, the separation of the ammonia from the mixture (II) can be effected by methods known per se for the separation of materials, such as extraction or, preferably, distillation, or a combination of such methods.

The distillation can advantageously be carried out at bottom temperatures of 60 to 220° C., especially of 100 to 220° C. The pressure, measured at the top of the distillation performance [sic], is conventionally set at 2 to 30 bar absolute.

Suitable apparatuses are those conventionally used for distillation, for example the ones described in Kirk-Othmer, Encyclopedia of Chemical Technology, 3rd Ed., Vol. 7, John Wiley & Sons, New York, 1979, pages 870–881, such as sieve-plate columns, bubble-cap columns or packed columns.

The distillation can be carried out in several columns, such as 2 or 3, but advantageously in a single column.

In step c), water and optionally liquid diluents are removed from the mixture (III) to give a mixture (IV) containing caprolactam, high-boiling components and low-boiling components.

If a liquid diluent has been used in step a), water and liquid diluent can be separated off simultaneously in step c) or the water can be separated off before or after the liquid diluent.

In principle, the water can be separated from the mixture (III) by methods known per se for the separation of materials, such as extraction, crystallization or, preferably, distillation, or a combination of such methods.

The distillation can advantageously be carried out at bottom temperatures of 50 to 250° C., especially of 100 to 230° C.

Suitable apparatuses are those conventionally used for distillation, for example the ones described in Kirk-Othmer, Encyclopedia of Chemical Technology, 3rd Ed., Vol. 7, John Wiley & Sons, New York, 1979, pages 870–881, such as sieve-plate columns, bubble-cap columns or packed columns.

The distillation can be carried out in several columns, such as 2 or 3, but advantageously in a single column.

A heat-coupled multistage separation of the water and optionally the liquid diluent is particularly preferred.

Before the mixture (IV) is introduced into step d), it is appropriate to separate off the low-boiling component [sic] and high-boiling component [sic], advantageously only the high-boiling components, especially neither the low-boiling component [sic] nor the high-boiling component [sic] and particularly advantageously only the low-boiling components from the mixture (IV).

If the low-boiling components and high-boiling components are separated from the mixture, the low-boiling components can be separated off before, after or together with the high-boiling components.

In the case where the low-boiling component [sic] and high-boiling component [sic], or only the high-boiling component [sic], or only the low-boiling component [sic], are separated off, the separation can be effected in principle by methods known per se for the separation of materials, such as extraction, crystallization or, preferably, distillation, or a combination of such methods.

The distillation can advantageously be carried out at bottom temperatures of 50 to 250° C., especially of 100 to 230° C. The pressure, measured at the top of the distillation performance [sic], is conventionally set at 1 to 500 mbar absolute, preferably 5 to 100 mbar absolute.

Suitable apparatuses are those conventionally used for distillation, for example the ones described in Kirk-Othmer, Encyclopedia of Chemical Technology, 3rd Ed., Vol. 7, John Wiley & Sons, New York, 1979, pages 870–881, such as sieve-plate columns, bubble-cap columns or packed columns.

The distillation for separating off the low-boiling components can be carried out in several columns, such as 2 or 3, but advantageously in a single column.

The distillation for separating off the high-boiling components can be carried out in several columns, such as 2 or 3, but advantageously in a single column.

In step d), a solid (V) containing caprolactam is obtained from the mixture (IV) by partial crystallization, the proportion by weight of caprolactam in the solid (V) being greater than in the mixture (IV).

The sum of the contents of high-boiling and low-boiling components, not including water and organic diluents, in the mixture (IV) used in step d) is advantageously at least 100 ppm by weight, preferably 200 ppm by weight, particularly preferably at least 500 ppm by weight and especially at least 1000 ppm by weight, based on the mixture (IV).

The crystallization can be effected batchwise or continuously.

The crystallization can be effected with the addition of an aid such as an organic or inorganic liquid diluent, for example water, but preferably without the addition of an aid.

The crystallization can be effected in one or more stages, such as two, three or four stages, preferably one stage. In another preferred embodiment of the invention, the crystallization can be effected as fractional crystallization.

In the case of fractional crystallization, all the stages producing a crystalline product (caprolactam) which is purer than the initial crude product (crude caprolactam) are conventionally called purification stages, and all the other stages are conventionally called refining stages. It is advisable here to operate multistage processes according to the countercurrent principle, whereby, after the crystallization in each stage, the crystalline product is separated from the remaining liquid phase ("mother liquor") and transferred to the appropriate stage with the next highest degree of purity, the crystallization residue being transferred to the appropriate stage with the next lowest degree of purity.

Advantageously, the temperature of the solution or melt during crystallization is not higher than the melting point of caprolactam (70° C.) and is preferably between –10 [sic] and the melting point of caprolactam and especially between 20 [sic] and the melting point of caprolactam. The solids content in the crystallizer is conventionally between 0 and 70 g, preferably between 30 and 60 g, per 100 g of charge.

In another advantageous embodiment of the invention, the crystallization is effected in apparatuses in which the crystals grow on cooled surfaces in the crystallization apparatus, i.e. are fixed in the apparatus (e.g. layer crystallization process from Sulzer Chemtech (Switzerland) or static crystallization process from BEFS PROKEM (France)).

The crystallization can also be effected by cooling apparatus walls or by evaporating a solution of the crude caprolactam under reduced pressure. Five to 30% by weight solutions of crude caprolactam in a liquid diluent, especially water, are particularly suitable for this purpose.

In the case of crystallization by cooling, the heat can be removed via scraped wall chillers connected to a stirred tank or an unstirred vessel. The crystal suspension can be circulated by means of a pump. A further possibility is to remove the heat via the wall of a tank with a wall-fitted stirrer. Another preferred embodiment of crystallization by cooling is the use of cooling disk crystallizers, e.g. those manufactured by Gouda (Holland). In another suitable variant of crystallization by cooling, the heat can be removed via conventional heat exchangers (preferably shell-and-tube or parallel-plate heat exchangers). In contrast to scraped wall chillers, tanks with wall-fitted stirrers or cooling disk crystallizers, these apparatuses do not possess a device for preventing layers of crystals from forming on the heat-transfer surfaces. If, during operation, a situation is reached where the resistance to heat transition due to the formation of layers of crystals becomes excessive, the conventional procedure is to switch over to a second apparatus. During the operating period of the second apparatus, the first apparatus can be regenerated (preferably by melting the layer of crystals or flushing the apparatus with unsaturated solution). If the resistance to heat transition in the second apparatus becomes excessive, the procedure is to switch back to the first apparatus, and so on. This variant can also be operated with more than two apparatuses in alternation. The crystallization can also be effected by conventional evaporation of the solution under reduced pressure.

The solid-liquid separation methods known per se are suitable for separating the mother liquor from the caprolactam which has crystallized out.

In one preferred embodiment of the invention, the crystals can be separated from the mother liquor by filtration and/or centrifugation. Advantageously, the filtration or centrifugation can be preceded by preliminary concentration of the suspension, for example by means of one or more hydrocyclones. Centrifuges known per se, which operate batchwise or continuously, are suitable for the centrifugation. It is most advantageous to use pusher centrifuges, which can be operated in one or more stages. Screen-conveyor centrifuges or helical-conveyor centrifuges (decanters) are also suitable. The filtration can advantageously be effected by means of suction filters, which can be operated batchwise or continuously and with or without a stirrer, or by means of belt filters. The filtration can generally be carried out under superatmospheric pressure or under reduced pressure.

During and/or after the solid-liquid separation, provision can be made for further process steps to increase the purity of the crystals or crystal cake. In one particularly advantageous embodiment of the invention, the separation of the crystals from the mother liquor is followed by washing and/or sweating of the crystals or crystal cake in one or more stages.

In the case of washing, the amount of washing liquor should preferably be between 0 and 500 g per 100 g of crystalline product, preferably between 30 and 200 g per 100 g of crystalline product.

Suitable washing liquors are organic or inorganic liquids or mixtures of such liquids, examples of preferred washing liquors being a) in the case where a liquid diluent has been used in the crystallization of step d), said liquid diluent, b) a melt of a crystalline product obtained in a crystallization stage of step d), c) a mother liquor obtained in a crystallization stage of step d), or d) a melt of an educt used in a crystallization stage of step d).

The washing can be effected in apparatuses conventionally used for this purpose. It is advantageous to use wash columns, in which the separation of the mother liquor and the washing take place in one apparatus, centrifuges, which can be operated in one or more stages, or suction filters or belt filters. The washing can be effected on centrifuges or belt filters in one or more stages, it being possible for the washing liquor to be conveyed in countercurrent to the crystal cake.

Particularly in the case of crystallization without the addition of an aid, the washing liquor can be recycled into the crystallization, optionally after impurities have been separated off.

Sweating is conventionally understood as meaning a local melting of contaminated regions. The amount of sweating should advantageously be 0.1 to 90 g of melted crystalline product per 100 g of crystalline product prior to sweating, preferably 5 to 35 g of melted crystalline product per 100 g of crystalline product. It is particularly preferred to carry out the sweating on centrifuges or belt filters. It may also be appropriate to combine washing and sweating in one apparatus.

Particularly in the case of crystallization without the addition of an aid, the mother liquor can be recycled into the crystallization, optionally after impurities have been separated off.

Caprolactam can be obtained in a purity of at least 99.90% by weight, preferably 99.90 to 99.99% by weight, by the present process.

The caprolactam obtainable by the process according to the invention can be used for the preparation of polyamides like polycaprolactam.

We claim:

1. A process for the preparation of caprolactam, wherein a) a mixture (I) containing 6-aminocapronitrile and water is reacted in the gas phase, in the presence of a catalyst, to give a mixture (II) containing caprolactam, ammonia, water, high-boiling components and low-boiling components, b) ammonia is then removed from the mixture (II) to give a mixture (III) containing caprolactam, water, high-boiling components and low-boiling components, c) water is then removed from the mixture (III) to give a mixture (IV) containing caprolactam, high-boiling components and low-boiling components, and d) a solid (V) containing caprolactam is then obtained from the mixture (IV) by crystallization, the proportion by weight of caprolactam in the solid (V) being greater than in the mixture (IV).

2. A process as claimed in claim 1 wherein the mixture (I) additionally contains an inert gaseous diluent.

3. A process as claimed in claim 2 wherein titanium dioxide, aluminum oxide or lanthanum phosphate is used in step a) as the catalytically active component of the catalyst.

4. A process as defined in claim 1, wherein the low boilers are separated between steps c) and d).

5. A process as defined in claim 1, wherein the high boilers are separated between steps c) and d).

6. A process as defined in claim 1, wherein the low boilers and high boilers are separated between steps c) and d).

7. A process as defined in claim 1, wherein the sum of the contents of high boilers and low boilers in mixture (IV) used in step d), calculated without water and any diluent still present, is at least 100 ppm by weight.

8. A process as defined in claim 1, wherein crystallization in step d) is carried out in the absence of auxiliary agents.

9. A process as defined in claim 1, wherein crystallization in step d) is carried out on a cooled surface, on which solid (V) grows.

10. A process as defined in claim 1, wherein the mother liquor obtained after crystallization in step d) is mixed with mixture (IV) and recycled to step d).

11. A process as defined in claim 1, wherein crystallization in step d) is carried out batchwise.

* * * * *